US012790583B2

(12) United States Patent
Lee

(10) Patent No.: US 12,790,583 B2
(45) Date of Patent: Nov. 10, 2026

(54) METHOD OF ENHANCING ETHANOL FERMENTATION

(71) Applicant: Lytegro Limited, Leicester (GB)

(72) Inventor: Andrew John Lee, Leicester (GB)

(73) Assignee: LYTEGRO LIMITED, Leicester (GB)

( * ) Notice: Subject to any disclaimer, the term of this patent is extended or adjusted under 35 U.S.C. 154(b) by 947 days.

(21) Appl. No.: 17/911,312

(22) PCT Filed: Mar. 16, 2021

(86) PCT No.: PCT/GB2021/050651
§ 371 (c)(1),
(2) Date: Sep. 13, 2022

(87) PCT Pub. No.: WO2021/186164
PCT Pub. Date: Sep. 23, 2021

(65) Prior Publication Data

US 2023/0112015 A1 Apr. 13, 2023

(30) Foreign Application Priority Data

Mar. 16, 2020 (GB) ...................................... 2003765

(51) Int. Cl.
*C12N 1/38* (2006.01)
*C12N 1/185* (2026.01)
*C12P 7/06* (2006.01)

(52) U.S. Cl.
CPC ............... *C12N 1/38* (2013.01); *C12N 1/185* (2021.05); *C12P 7/06* (2013.01)

(58) Field of Classification Search
None
See application file for complete search history.

(56) References Cited

FOREIGN PATENT DOCUMENTS

WO 2007052081 A2 5/2007
WO WO-2013067305 A1 * 5/2013 ............... C12N 1/38

OTHER PUBLICATIONS

International Search Report for international application No. PCT/GB2021/050651, Jun. 11, 2021, 2 pages.
Rosario et al., Continuous-Flow Fermentation of Banana Fruit Pulp Sugar into Ethanol by Carrageenan-Immobilized Yeast, Biotechnology Letters, vol. 7, No. 11, 1985, pp. 819-820.

* cited by examiner

*Primary Examiner* — Christian L Fronda
(74) *Attorney, Agent, or Firm* — Kilyk & Bowersox, P.L.L.C.

(57) ABSTRACT

A method of forming an ethanol fermentation enhancement mixture is provided and involves: hydrating a dried yeast with at least 0.1% Baclyte or a banana extract by volume, and a yeast growth media to produce a pre-fermentation mixture; and maintaining the pre-fermentation mixture at a temperature between 20° C. and 40° C. for between 30 minutes and 8 hours. Alternatively, the method involves: providing a solution of hydrated activated yeast; supplementing the solution of hydrated activated yeast with 0.1% to 25% BacLyte or banana extract by volume; and maintaining the solution of hydrated activated yeast at a temperature between 20° C. and 40° C. for between 30 minutes and 8 hours. A fermentation method involves preparing an ethanol enhancement mixture; adding the mixture to a bulk fermentation mixture containing a sugar source; and maintaining the bulk fermentation mixture at temperature of between 2° C. and 40° C. to allow fermentation of the sugar source to ethanol.

3 Claims, 6 Drawing Sheets

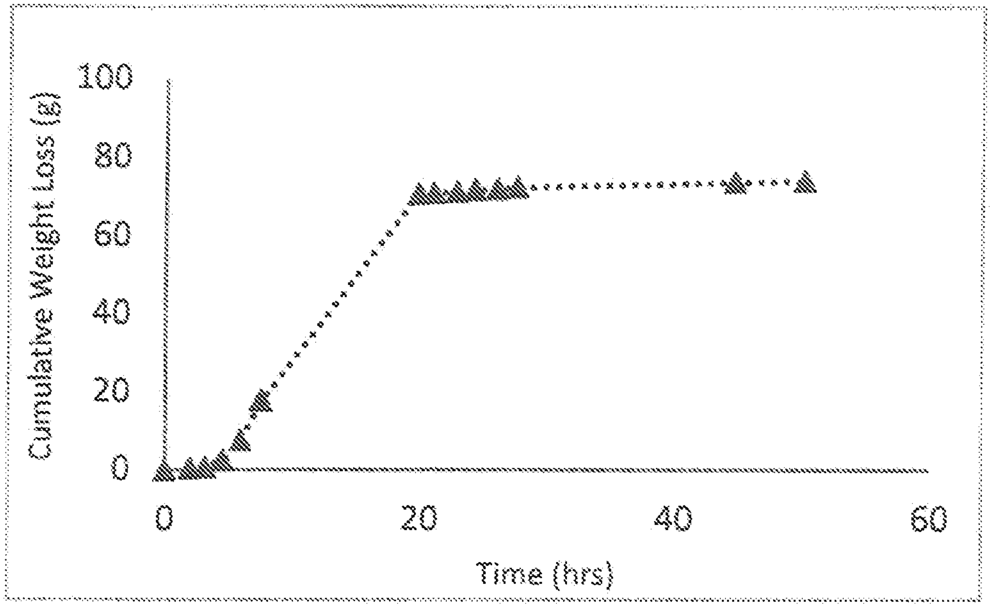
Figure 1: Mean cumulative weight loss over time in control fermentation.
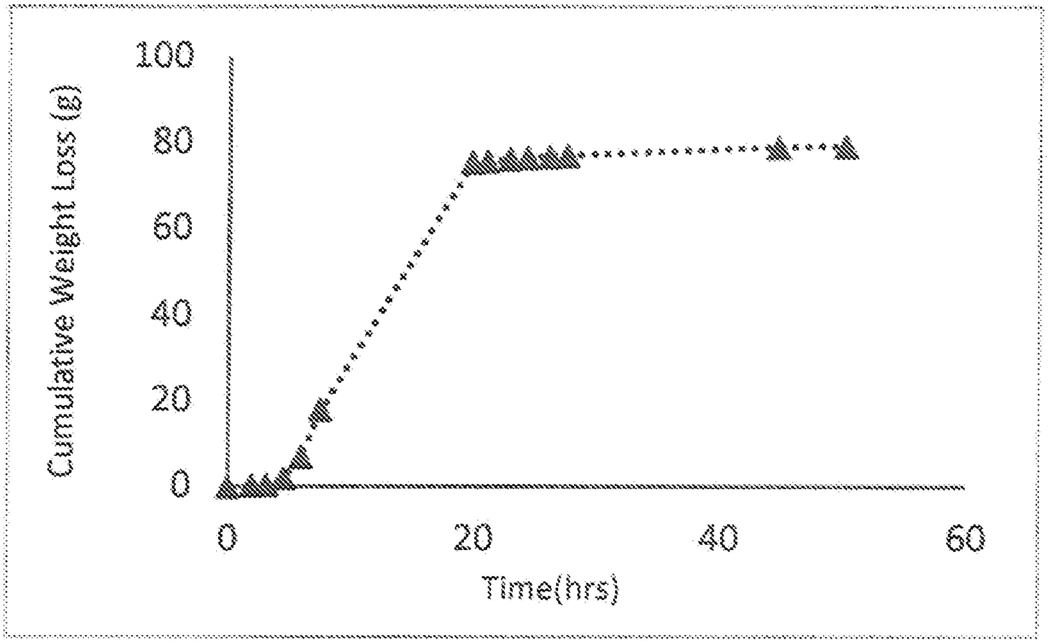
Figure 2: Mean cumulative weight loss over time in water hydrated fermentation.

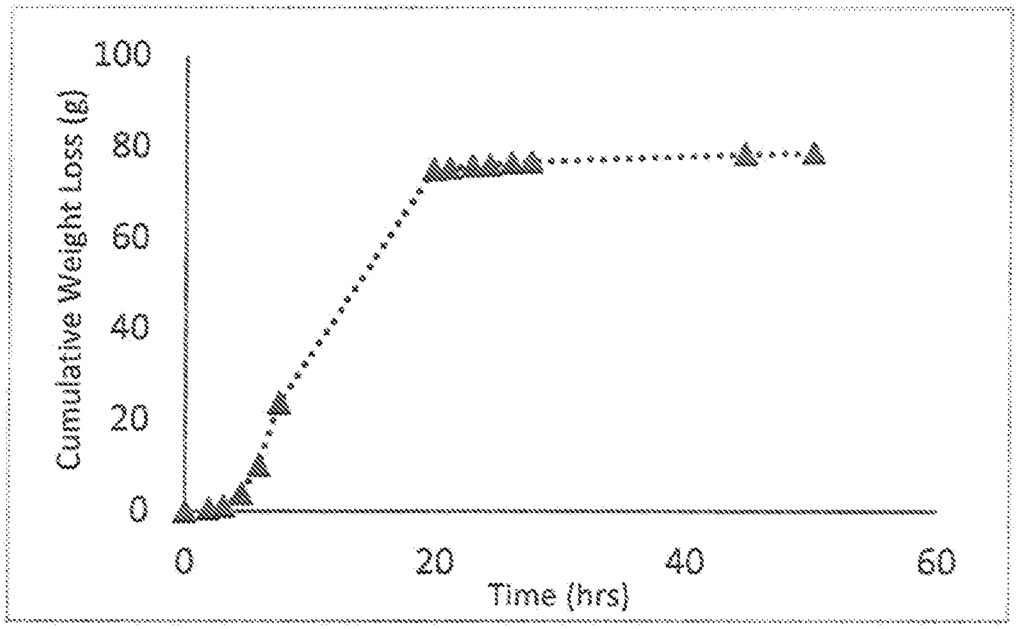
Figure 3: Mean cumulative weight loss in water & BacLyte fermentation.
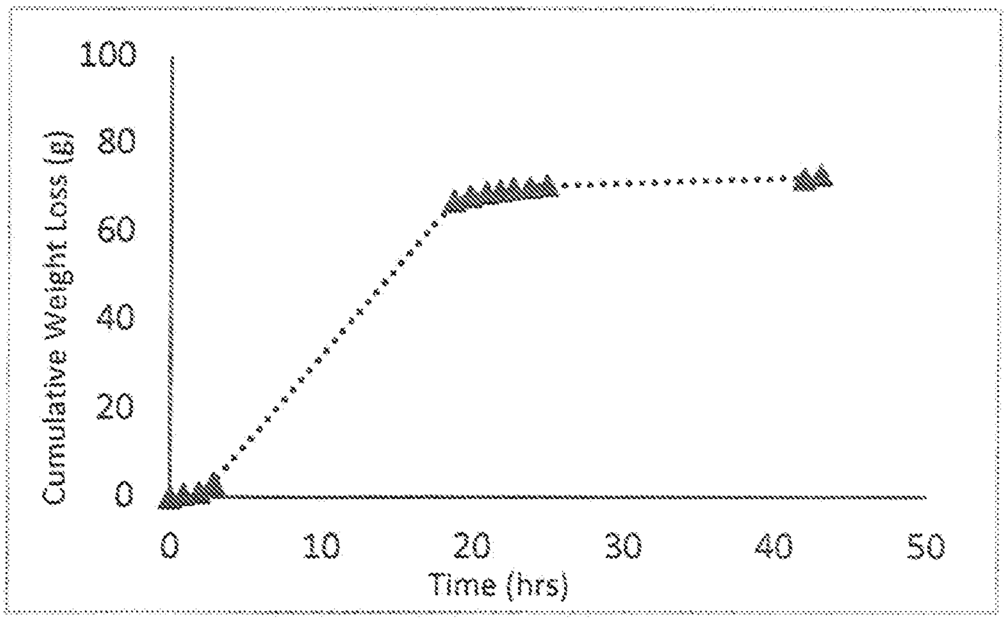
Figure 4: Mean cumulative weight loss in YPD fermentation.

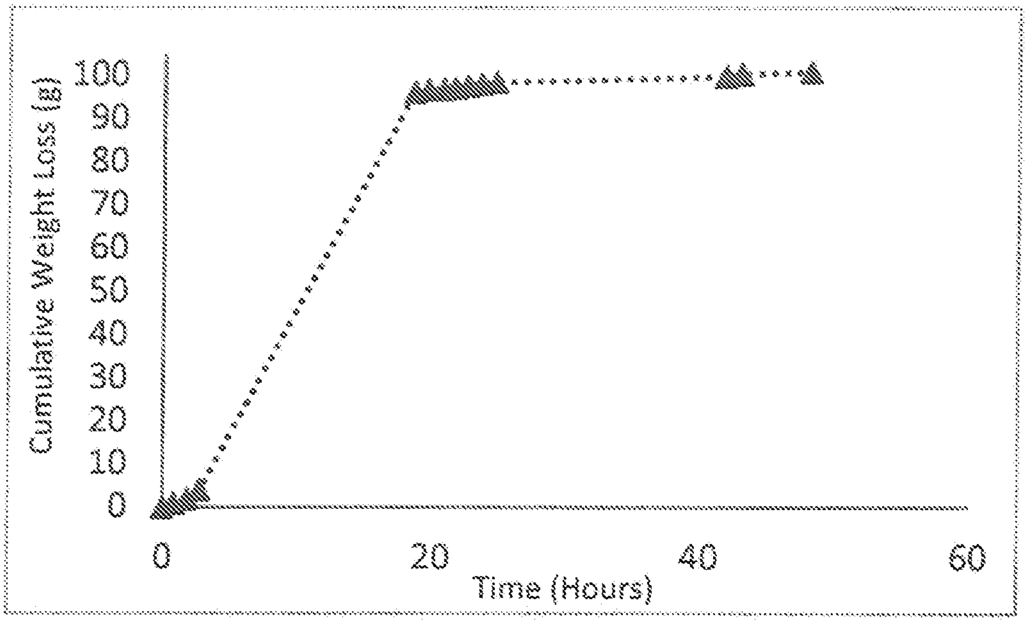
Figure 5: Mean cumulative weight loss in YPD & BacLyte Fermentation.
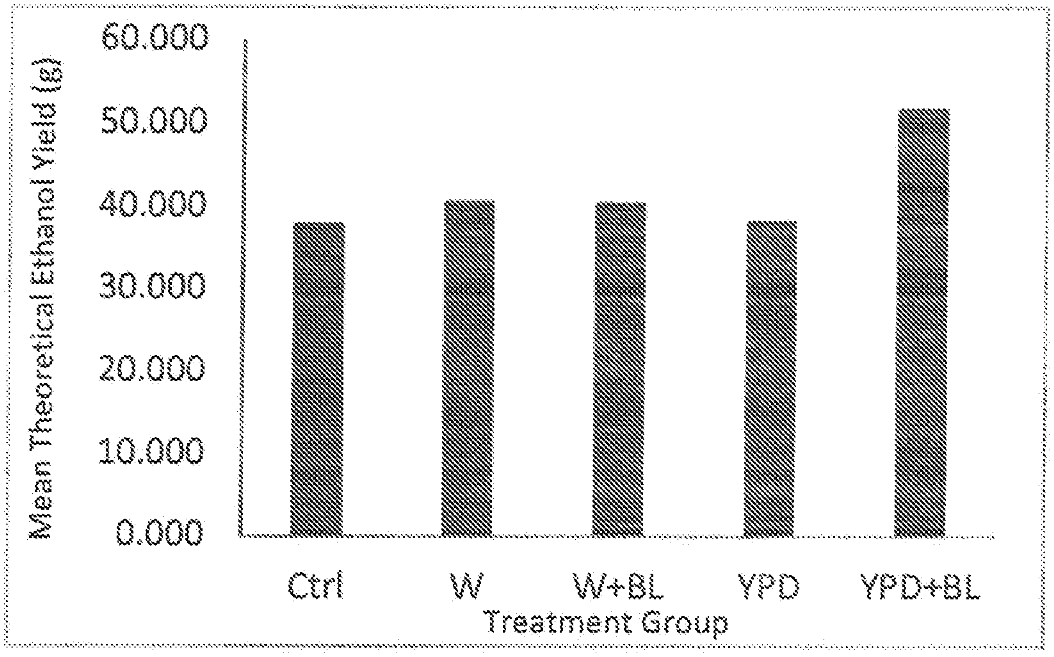
Figure 6: Theoretical mean alcohol yields from fermentations.

METHOD OF ENHANCING ETHANOL FERMENTATION

FIELD OF THE INVENTION

The present invention relates to the production of ethanol from sugar via fermentation and provides a method of enhancing the fermentation process.

BACKGROUND TO THE INVENTION

Ethanol is consumed as alcohol in a variety of different beverages, for example beers and ciders, wines and distilled spirits such as vodkas, gins, rums and whiskies. In all of those beverages the ethanol is produced from natural sugar sources via a fermentation process using yeast. Ethanol also has a further use as a biofuel, which is also generally produced via a fermentation process.

Yeast is a facultative anaerobe; meaning that it can survive and grow in both aerobic or anaerobic conditions. The presence of oxygen determines the metabolic fate of a cell. In terms of a yeast cell, its survival, growth and metabolism is optimal in the presence of oxygen, where it will rapidly grow to high densities and will convert glucose in its environment to carbon dioxide and water. Under anaerobic conditions however yeast grows much more slowly and to lower cell densities and glucose is incompletely metabolised to produce ethanol and carbon dioxide. The anaerobic growth of yeast is the basis of the fermentation process.

As a fermentation proceeds there is an increase in ethanol concentration within a fermentation mixture. This process continues up until the point where high ethanol concentrations start to become toxic and begin to kill the yeast cells. Commercial brewing and distilling yeast strains have been bred for attractive traits such as minimising the lag-phase of a fermentation, accelerated metabolic activity, which improves the rate ethanol is produced, and increased tolerance to alcohol, so that yeast cells can survive in higher concentrations of ethanol thereby facilitating increased yields of ethanol from each fermentation. Brewing and distilling yeasts typically tolerate ethanol levels of below 6% alcohol by volume (ABV) in culture with them starting to be killed off as ethanol concentrations exceed this level; although some commercial strains of yeasts have been shown to be able to tolerate ethanol levels of up to 15% ABV.

The speed of a fermentation process depends on the environmental conditions of the fermentation mixture such as temperature, the sugar content of the fermentation mixture, the amount of yeast, and the alcohol concentration of the fermentation mixture as the process continues.

Beer and cider fermentations differ in some respects from both wine and distilling fermentations insofar as brewers do not want beer and ciders to contain maximal levels of alcohol. As such, the fermentation process for beer and cider fermentation is normally halted once the ABV has reached around 4-6%. For beer and cider brewers there is a desire to optimise the speed and efficiency of the fermentation process in order to reach the required ABV as quickly as possible, rather than to increase the overall yield of ethanol. Distillers however seek to optimise fermentation speed and efficiency whilst producing the most amount of ethanol possible from each fermentation; as it is this ethanol which, when extracted from the fermentation, forms the basis of their products. As such, the improvement of the overall yield of ethanol from each fermentation is very commercially attractive to distillers.

Generally, commercial fermentations consist of two separate processes, an initial yeast propagation stage and then a full fermentation stage where alcohol is produced. The propagation stage is required to provide sufficient amounts of yeast cells in a metabolically active state to enable the efficient fermentation of a feedstock. Propagation can either be performed as a separate process outside of a fermentation; with the resultant primed yeast then being added into a fermentation mixture or it can occur in situ to a fermentation; where typically dried yeast is added to a fermentation in the amount required and then left to metabolically resuscitate over the lag-phase i.e. the first four to six hours of the fermentation.

In an initial yeast propagation stage yeast is generally cultured in a suitable growth media and environment. This process allows an initially small population of metabolically quiescent cells (typically in a dried form) to be resuscitated to become metabolically active and to then enter a replicative phase which will result in a much larger population suitable for use in the subsequent full fermentation stage. Conditions of the initial yeast propagation stage should be such that a maximal amount of yeast is produced which provides optimal fermentation performance in the subsequent full fermentation stage. To achieve this, yeast propagation stages are performed under aerobic conditions which facilitates the production of unsaturated fatty acids and sterols which form a cell membrane of the yeast. These molecules are important for both growth and fermentation and serve as a means of storing oxygen within the yeast cells. They are also necessary for increasing yeast cell mass (growth), improving the overall uptake of nutrients, and determining alcohol tolerance of the yeast cells subsequently used in the full fermentation stage. Oxygen also stimulates synthesis of molecules necessary for yeast to metabolize and take up maltose, the primary sugar in wort, which is the feedstock for production of beers, ciders and distilled spirits.

It is important in any yeast propagation stage that the yeast is first hydrated and cultured in a growth media that is supportive of its growth and is neither toxic nor detrimental to growth or flavour when added to the subsequent full fermentation stage. Yeast is cultured in a suitable growth media at an optimum growth temperature in order for it to propagate. Suitable growth mediums typically include peptone, yeast extract, and dextrose or glucose. There are many variant commercial growth mediums on the market with slightly differing amounts of these ingredients, but they are generally referred to as YPD media. YPD media contains either glucose or dextrose as a sugar source with yeast extract and the peptone included to provide nitrogen and the amino acids necessary for growth. The yeast extract also provides vitamin B complex. YPD media has been reliably found to provide excellent propagation of yeast in appropriate conditions.

Alternatively, propagation of yeast may be included in a bulk fermentation process in which the dried yeast is simply added to a bulk fermentation mixture without being previously hydrated or cultured. In this case, there is an initial time period during which little or no fermentation occurs whilst the yeast propagates in situ within the bulk fermentation mixture. This initial time period is called a lag-phase and typically with brewing and distilling yeasts lasts around four to six hours before the yeast then enters a replicative phase. Shortening of this lag phase is desirable for both beer and cider brewers as well as distillers.

In some fermentations yeast is utilised from previous fermentations or from a continuous propagation source. In these cases, in contrast to the propagation of dried yeast, the yeast is already hydrated and activated and there may be sufficient amounts to be added directly to a bulk fermentation to immediately begin fermentation. Therefore, when such sources of live and activated yeast are used there is no need to hydrate and culture the yeast or for a propagation stage. Instead, a suitable amount of live, activated yeast is added to the bulk fermentation mixture and the yeast enters the replicative phase almost immediately. In such cases, there is generally no use of growth media with the yeast.

EP1945763 describes an extract for promoting the growth of bacteria. The extract is a crude banana extract that has particular use for promoting the growth of lactic acid bacteria. The extract is defined as an extract obtained from Musa spp, the extract being produced by blending at least a portion of a Musa fruit, preferably bananas, in a suitable diluent, in the absence of addition of further supplements, and autoclaving the extract at 121° C. at 103 kpa for 15 minutes; and the extract being present in the medium at a concentration of 0.01-10%. References in the present application to a "banana extract" are understood to be references to the extract of EP1945763.

EP2773744 discloses a supplement for promoting the growth of bacteria and yeasts. This supplement can be used to promote the growth of yeast. In particular, EP2773744 discloses methods utilising the supplement to provide an enhanced production of microorganisms, including yeast. This supplement can provide an improved production of yeast and other micro-organisms. The supplement disclosed in EP2773774 is a banana plant extract that is prepared according to the method disclosed therein and is being commercialised under the name BacLyte. EP2772744 shows at FIGS. 11 and 12 improved growth of yeast utilising the BacLyte supplemented media. FIG. 11 shows the growth of yeast in RPMI-1640 medium; a medium that does not usually support yeast growth as it does not contain the amino acids found in YPD media. The figure shows the growth of yeast in RPMI-1640 with and without supplementation with BacLyte and clearly demonstrates that the addition of the BacLyte supplement facilitates yeast growth in this otherwise unsupportive media. Thus, it is clear from EP2772744 that BacLyte supplement can provide improved growth of yeast in the absence of YPD media. FIG. 12 shows the growth of yeast in a 10% molasses solution with and without BacLyte. In the absence of BacLyte yeast growth is small, with the supplementation of BacLyte yeast growth is much higher.

In both FIG. 11 and FIG. 12 of EP2772744 it has been shown that BacLyte supplementation can provide excellent propagation of yeast in the absence of YPD. EP2772744 suggests that BacLyte supplementation allows the use of alternative growth media for yeast to avoid the need to include amino acids, which may interfere with downstream processing of the yeast, see paragraphs [0043] and [0044]. That is, according to the teaching of EP2772744, BacLyte supplementation allows the use of growth media other than YPD

SUMMARY OF THE INVENTION

A first embodiment of the present invention provides a method of forming an ethanol fermentation enhancement mixture comprising the steps of:

hydrating a dried yeast with at least 0.1% Baclyte or 0.1% of a banana extract according to EP1945763, and a YPD media to produce a pre-fermentation mixture; and heating the pre-fermentation mixture to between 25° C. and 40° C. for between 30 minutes and 8 hours to form the enhancement mixture.

As set out above, BacLyte is a supplement that has been found to promote the growth of various microorganisms, including yeast. BacLyte supplementation has previously been found to allow the use of media other than YPD for the growth of yeast According to the present invention, it has been found that the supplementation of YPD media with BacLyte for yeast is superior to the use of either BacLyte on its own or YPD on its own. Banana extract according to EP1945763 has been used to promote bacterial growth. Surprisingly, the combination of either BacLyte or a banana extract according to EP1945763 and YPD has been found to be more advantageous than would be reasonably be expected from their use in isolation from one another. In particular, the combination of BacLyte or a banana extract according to EP1945763 and YPD results in greater propagation of the yeast and propagation at a faster rate during the method of the present invention. Further, it has been found that yeast propagated from a pre-fermentation mixture containing BacLyte or a banana extract according to EP1945763 and a YPD media has an improved fermentation efficiency and an increased alcohol tolerance when used in a subsequent bulk fermentation. This means that the fermentation efficiency of bulk fermentation stages utilising the fermentation enhancement mixture according to the method of the present invention is better than bulk fermentation stages utilising yeast propagated according to the prior art.

The first embodiment of the method of the present invention can use any suitable yeast strain. All yeasts currently used in commercial fermentation are expected to be able to be used in the method of the present invention. The yeast may be *Saccharomyces cerevisiae*, for example Safspirit HG-1 produced by Fermentis or any other commercially available equivalent.

According to the first embodiment of the method of the present invention the mixture is maintained at a temperature of between 20° C. and 40° C. It may be advantageous that the mixture is maintained at a temperature between 32° C. and 38° C. or a temperature between 20° C. and 25° C. depending upon the strain of yeast. The mixture may be maintained at a temperature of approximately 35° C.

In the first embodiment of the method of the present invention the amount of BacLyte or banana extract may be between 0.1% and 25% by volume, between 0.1% and 20%, or between 0.1% and 15%. The amount of BacLyte or banana extract in the pre-fermentation mixture may be between 0.5% and 1.0% by volume. The amount of BacLyte or banana extract in the pre-fermentation mixture may be Between 1.0% and 4.0%, for example between 1.0% and 2.0%, between 2.0% and 3.0%, or between 3.0% and 4.0%. The amount of BacLyte or banana extract in the pre-fermentation mixture may be 2.5%. Alternatively, the amount of BacLyte or banana extract in the pre-fermentation mixture may be between 4% and 12% by volume, for example 5%, 6%, 7%, 8%, 9%, 10%, or 11%. The amount of BacLyte or banana extract in the pre-fermentation mixture may be between 5% and 10%.

Any suitable YPD media or other media supportive of the growth of yeast, may be utilised in the method of the present invention. A suitable YPD media may comprise approximately 10% yeast extract, 20% peptone, and 20% dextrose, with the remainder being water. Other media supportive of the growth of yeast will be immediately apparent to the person skilled in the art. Some media supportive of the growth of yeast will comprise amino acids, the first embodiment of the method of the present invention is suitable for use with such media. Other media supportive of the growth of yeast does not comprise amino acids, the first embodiment of the method of the present invention is also suitable for use with such media.

The present invention also comprises the addition of 0.1% to 15% of Baclyte or a banana extract, for example 5% Baclyte or 5% banana extract to a wart mix i.e. a rolling yeast propagation mix. We would expect this to provide the same unexpected technical effect as the resulting mixture would be a combination of Baclyte or a banana extract and a nutrient rich media comprising a yeast.

The pre-fermentation mixture may be maintained at temperature for between 2 and 8 hours, for example between 3.5 and 4.5 hours, or between 5 and 8 hours. The pre-fermentation mixture may be maintained at temperature for approximately 4 hours. The length of time at which the pre-fermentation mixture is maintained at temperature may be dependent upon the metabolic rate of the yeast strain or strains in the pre-fermentation mixture. Some yeasts are metabolically slower than others and will require the fermentation mixture to be held at temperature for longer times. Yeast strains that are metabolically slower will typically be held at temperature for between 6 and 8 hours. Yeasts that are metabolically quicker will typically be held at temperature for between 2 and 6 hours.

As set out below, the Applicant has data to indicate that yeast propagated in the pre-fermentation mixture of the present invention has a greater alcohol tolerance, allowing greater concentrations of alcohol to be produced using the yeast before the effects of alcohol toxicity cause cell death. This effect is particularly advantageous as it can allow much greater efficiency of alcohol production. It is believed that this effect exists even where the yeast propagated in the pre-fermentation mixture is used in a bulk fermentation without further supplementation of BacLyte or banana extract.

A second embodiment of the present invention provides a method of forming an ethanol fermentation enhancement mixture comprising the steps of:

- providing a solution of hydrated activated yeast;
- supplementing the solution of hydrated activated yeast with 0.1% to 25% BacLyte or banana extract according to EP1945763 by volume; and
- maintaining the solution of hydrated activated yeast at a temperature between 20° C. and 40° C. for between 30 minutes and 8 hours to form the enhancement mixture.

The mixture may be supplemented with 0.1% to 25% BacLyte or banana extract or 0.1% to 20% BacLyte or banana extract or 0.1% to 15% BacLyte or banana extract.

The solution of hydrated activated yeast of the second embodiment of the invention may be provided from any suitable source. For example, the solution of hydrated activated yeast may be provided from a continuous propagation source of from a previous bulk fermentation source. Suitable sources of hydrated activated yeast will be immediately apparent to the person skilled in the art.

In the same manner as the previous embodiment, the alternative embodiment of the invention is advantageous in that it can provide yeast with a greater alcohol tolerance and greater activity due to the exposure of the yeast to BacLyte or a banana extract for a period of time. This yeast can then be used as an ethanol fermentation enhancement mixture and can provide any subsequent bulk fermentation utilising the fermentation enhancement mixture with improved fermentation characteristics. It is not necessary to supplement a subsequent bulk fermentation stage with BacLyte or banana extract, although this may be done if preferred.

The second embodiment of the method of the present invention can use any suitable yeast strain. All yeasts currently used in commercial fermentation are expected to be able to be used in the method of the present invention. The yeast may be *Saccharomyces cerevisiae*, for example Safspirit HG-1 produced by Fermentis or any other commercially available equivalent. The yeast may be any of the yeasts used in the four investigations described below.

According to the second embodiment of the method of the present invention the mixture is maintained at a temperature of between 20° C. and 40° C. It may be advantageous that the mixture is maintained at a temperature between 32° C. and 38° C. or a temperature between 20° C. and 25° C. depending upon the strain of yeast. The mixture may be maintained at a temperature of approximately 35° C.

According to the second embodiment of the method of the present invention the solution of hydrated activated yeast is supplemented with 0.1% to 15% BacLyte or banana extract by volume. The amount of BacLyte or banana extract may be between 0.5% and 1.0% by volume. The amount of BacLyte or banana extract may be Between 1.0% and 4.0%, for example between 1.0% and 2.0%, between 2.0% and 3.0%, or between 3.0% and 4.0%. The amount of BacLyte or banana extract may be 2.5%. Alternatively, the amount of BacLyte or banana extract may be between 4% and 12% by volume, for example 5%, 6%, 7%, 8%, 9%, 10%, or 11%. The amount of BacLyte or banana extract may be between 5% and 10%.

In contrast, to the first embodiment of the present invention, the second embodiment of the present invention is not concerned with the propagation of dried yeast, rather it exposes hydrated activated yeast to BacLyte or banana extract for a period of time between 30 minutes and 8 hours. Therefore, there is no requirement to supplement the solution of hydrated activated yeast with a media supportive of the growth of yeast, such as YPD. However, it may be advantageous to add such a media to the solution of hydrated activated yeast. In such circumstances any suitable YPD media or other media supportive of the growth of yeast, may be utilised in the method of the present invention. Any media suitable for use in the first embodiment of the method of the present invention will also be suitable for use in the second embodiment of the method of the present invention.

The solution of hydrated activated yeast supplemented with BacLyte or banana extract may be maintained at temperature for between 2 and 6 hours, for example between 3.5 and 4.5 hours, or between 5 and 8 hours. The solution of hydrated activated yeast supplemented with BacLyte or banana extract may be maintained at temperature for approximately 4 hours. The length of time at which the solution of hydrated activated yeast supplemented with BacLyte or banana extract is maintained at temperature may be dependent upon the metabolic rate of the yeast strain or strains in the pre-fermentation mixture. Some yeasts are metabolically slower than others and will require the fermentation mixture to be held at temperature for longer times. Yeast strains that are metabolically slower will typically be held at temperature for between 6 and 8 hours. Yeasts that are metabolically quicker will typically be held at temperature for between 2 and 6 hours.

An enhancement mixture comprising BacLyte or banana extract prepared according to a method present invention is particularly useful for enhancing fermentation. However, the enhancement mixture may be utilised for any process requiring the activity of yeast, including yeast fermentations, anaerobic digestion and baking processes.

The present invention also provides:

A fermentation method comprising the steps of:

i) preparing an enhancement mixture according to the present invention;

ii) adding the enhancement mixture to a bulk fermentation mixture containing a sugar source; and iii) maintaining the bulk fermentation mixture at temperature of between 2° C. and 40° C. to allow fermentation of the sugar source to ethanol.

Fermentation according to the method of the present invention has been found to provide a higher ethanol yield than fermentation using yeast propagated according to the prior art. In particular, the yeast contained in the enhancement mixture of the present invention is believed to have a higher alcohol tolerance, thereby allowing the fermentation to produce a higher concentration of alcohol at the end of the fermentation process as a consequence of the improved survivability of the yeast cells in the fermentation. Further, the fermentation has been found to occur at a faster rate. It is believed that this is due to the yeast in the enhancement mixture being more metabolically active as a result of its exposure to BacLyte or banana extract prior to addition to the bulk fermentation mixture. As will be readily appreciated a method of fermentation that provides fermentation at a faster rate and provides a higher maximum alcohol yield is significantly beneficial over the prior art.

The method of the fermentation of the present invention is particularly advantageous as it does not require supplementation of the bulk fermentation mixture with BacLyte or banana extract, something that was previously considered necessary in the prior art. Instead, the advantages of supplementation with BacLyte or banana extract have been found to occur through supplementation of the enhancement mixture regardless of whether the bulk fermentation mixture is also supplemented. This is advantageous in that BacLyte or banana extract is relatively expensive compared to other components of the fermentation mixture and is not currently produced in volumes suitable for use in bulk fermentation.

The sugar source of the present invention may be any suitable source including, but not limited to, molasses, potato starch, grain sources, and sugar cane sources. It is expected that the present invention will operate with substantially any sugar source that facilitates fermentation. Further examples of suitable starch and sugar-based ethanol feedstocks include but are not limited to agave, rice, and corn. A sugar source of the present invention may also be the breakdown of lignocellulose into more basic sugars by other micro-organisms in cellulosic ethanol feedstocks as utilised in anaerobic digestion processes.

Further the addition of BacLyte directly to bulk fermentation mixtures has been found to result in relatively high levels of ethyl acetate and isoamyl acetate, as compared to fermentation mixtures not comprising BacLyte. Isoamyl acetate has an intense banana-like odour and characteristic banana-like flavour. This is not unexpected as BacLyte is an aqueous solution of banana extract and it is believed that the BacLyte may have a role in the production of isoamyl acetate in fermentation mixtures. Ethyl acetate has a fruity odour with a brandy note and has a pleasant taste whilst diluted. Whilst neither compound is unpleasant in itself, if the alcohol from the fermentation mixture is intended for specific drinks then the presence of strongly flavoured compounds could be disadvantageous as those flavours will also be present in the final drink. Similarly, the addition of banana extract to a bulk fermentation mixture would also result in a liquid with a degree of banana flavouring. For example, the supplementation of bulk vodka fermentation mixture with BacLyte could result in a banana flavoured vodka, which is generally not preferred. By utilising BacLyte or banana extract in the pre-fermentation mixture alone, this issue is avoided as, after fermentation of the bulk fermentation mixture only low levels of ethyl acetate and isoamyl acetate are found to be present. Thus in embodiments of the method of fermentation according to the present invention the bulk fermentation mixture is not further supplemented with BacLyte or banana extract beyond the BacLyte or banana extract present in the enhancement mixture.

DRAWINGS

FIG. 1 is a graph showing the mean cumulative weight loss over time in control fermentation mixtures;

FIG. 2 is a graph showing the mean cumulative weight loss over time in fermentation mixtures comprising a hydrated yeast enhancement mixture;

FIG. 3 is a graph showing the mean cumulative weight loss over time in fermentation mixtures comprising a hydrated yeast enhancement mixture containing BacLyte;

FIG. 4 is a graph showing the mean cumulative weight loss over time in fermentation mixtures comprising a hydrated yeast enhancement mixture containing YPD;

FIG. 5 is a graph showing the mean cumulative weight loss over time in fermentation mixtures comprising a hydrated yeast enhancement mixture containing YPD and BacLyte;

FIG. 6 is a graph showing the theoretical mean alcohol yields for the samples of FIGS. 1 to 5;

FIRST INVESTIGATION

Figure 7:
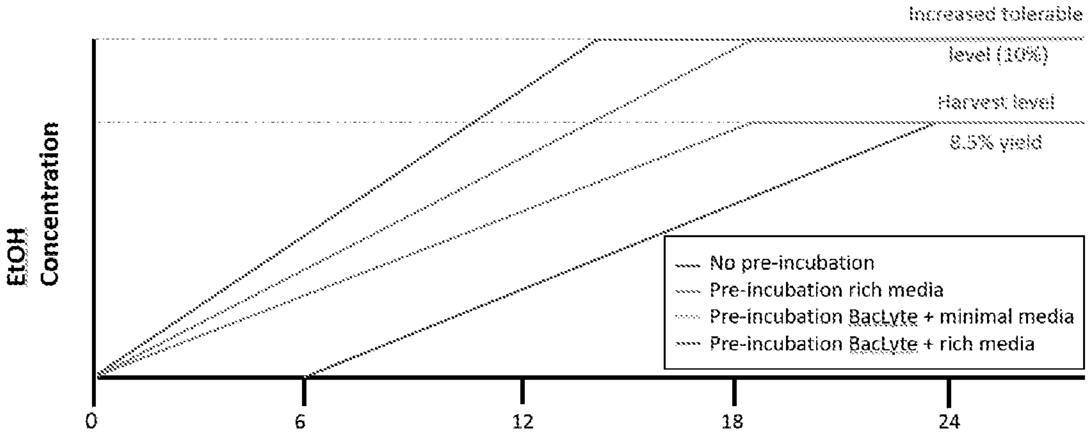
FIG. 7 is a graph showing the expected increase in ethanol concentration with time for four different bulk fermentation mixtures.

The results of a first investigation into the use of BacLyte to form an enhancement mixture are shown in FIGS. 1 to 7. In particular, the following investigation was carried out:

Preparation of Enhancement Mixture

A *Saccharomyces cerevisiae* distiller's yeast (Safsprit HG-1 produced by Fermetis) was used to prepare four samples of enhancement mixture in triplicate. Each sample was subject to different hydration regimes, along with a control sample in which the yeast was not hydrated. The hydration regime of each sample was as follows:

TABLE 1

| Sample | Components |
|---|---|
| Control (C) | Dry yeast only |
| Water (W) | Dry yeast & distilled water |
| Water & BacLyte (WB) | Dry yeast, distilled water, 5% BacLyte by volume |
| Water & YPD (WY) | Dry yeast, YPD |
| Water, YPD, & BacLyte (WYB) | Dry yeast, YPD, and 5% BacLyte by volume |

Each sample was hydrated for 4 hours and maintained at a temperature of 35° C. Each sample contained 0.5 g of Safsprit HG-1 yeast. The resulting enhancement mixtures were then utilised in fermentation of a fermentation mixture containing sugar. In the samples containing YPD, the sample consisted of 10% yeast extract, 20% peptone, 20% dextrose (by volume), excluding any BacLyte component.

Preparation of Fermentation Mixture

Maris Piper potatoes were used as the base sugar source for the fermentation mixture. The potatoes were rinsed and scrubbed thoroughly to remove any dirt or debris from their surface. They were then finely chopped and then crushed using a blender. A potato and water mixture was produced with a ratio of 1 kg of potato per litre of water. The mixture was homogenised and decanted into 2 litre bottles.

In order to gelatinise the starch in each bottle, each bottle was heated at 115° C. for 14 minutes. Exogeneous enzymes were then added according to accepted dosage instructions. Specifically, distiller's high temperature α-amylase was added at 1 g per litter, stirred into each bottle at 85° C. and the bottle was then held at between 85° C. and 90° C. for 1 hour. After cooling to 60° C., distiller's glucoamylase was then added to each sample at 1.4 g per litre and the bottles were then held at this temperature at 1 hour. The bottles were then cooled to 30° C. to form the fermentation mixture.

Fermentation

The enhancement mixtures were added to the bottles at 30° C. and the bottles were maintained at this temperature. Fermentation was monitored by recording the weight changes of each bottle and by recording the specific gravity of each fermentation mixture during fermentation.

Subsequent Processing

Upon completion of the fermentation the solid matter was removed from each fermentation mixture utilising a laboratory sieve stack containing wire mesh sieve layers with holes of 1400 μm and 710 μm respectively. From each fermentation mixture, one litre of liquid was obtained. At this point, the liquid from the triplicates of each sample was combined to produce three litres of liquid, one for each different sample.

Each liquid was then distilled in a 5 litre copper still to produce low wines. The alcohol content of the low wines produced from the distillation of the liquids was monitored and distillation continued until the alcohol production of the low wines reached 1% ABV.

Subsequently the low wines were then distilled in a 2 litre copper still. The first 10 ml was collected as foreshots. The alcohol content of each foreshot was measured using an Anton-Paar DMA 100 handheld density meter. The following portion of the distillate was collected as hearts. The percentage of alcohol was monitored throughout the distillation and the hearts were collected until there was a 12.5% decrease in ABV from the ABV of the corresponding foreshot. The residual liquid was discarded.

Results

The mean cumulative weight loss of each pre-fermentation sample is shown in FIGS. 1 to 5. The weight loss per hour of each sample was as follows:

TABLE 2

| Time (hrs) | C | W | WB | WY | WYB |
|---|---|---|---|---|---|
| 0-2 | 0.198 ± 0.121 | 0.121 ± 0.078 | 0.309 ± 0.128 | 0.503 ± 0.084 | 0.764 ± 0.135 |
| 2-3 | 0.114 ± 0.045 | 0.073 ± 0.035 | 0.138 ± 0.035 | 0.753 ± 0.101 | 0.778 ± 0.017 |
| 3-19 | 2.662 ± 0.005 | 2.906 ± 0.236 | 2.595 ± 0.236 | 3.548 ± 1.073 | 5.115 ± 1.585 |
| 19-21 | 0.010 ± 0.005 | 0.014 ± 0.005 | 0.016 ± 0.003 | 0.033 ± 0.001 | 0.017 ± 0.004 |
| 21-23 | 0.016 ± 0.007 | 0.017 ± 0.004 | 0.013 ± 0.004 | 0.015 ± 0.006 | 0.019 ± 0.008 |
| 24-44 | 0.030 ± 0.003 | 0.044 ± 0.006 | 0.040 ± 0.006 | 0.032 ± 0.010 | 0.023 ± 0.004 |

The difference in the rate of weight loss in the WY and WYB samples in the first two hours as compared to the C, and W samples was found to be statistically significant ($p<0.05$). Furthermore the weight loss of the WYB samples was significantly higher than the rates of the weight loss of WB and WY samples in the first two hours. The weight loss in the third hour of fermentation decreased in the C, W, and WB samples but increased in the WY and WYB samples. The weight loss in the third hour was significantly higher in the WY and WB samples than those of the C, W, and WB samples. Weight loss increased significantly in all samples in the 3-19 hour time period. Again, the highest weight loss occurred in the WYB sample and this weight loss was significantly higher than any other sample. After 19 hours the hourly rate of weight loss decreased markedly. This reduced hourly weight loss continued in the subsequent time periods.

From the measured weight loss it is possible to calculate a theoretical yield value of ethanol for each sample from the cumulative weight loss. In particular, a theoretical equation for the partial oxidation of glucose through the fermentation pathway, taking into consideration the molecular weight of the respective components, states that per kg of glucose, there is a theoretical yield of 0.489 kg of $CO_2$ and 0.511 kg of glucose (Daoud & Searle, 1990). Using these yield values, ethanol and $CO_2$ production can be calculated from the cumulative weight loss. The results of this calculation are shown in FIG. 6 and set out in table 3:

TABLE 3

| Sample | Mean Ethanol Yield |
|---|---|
| C | 37.8 g |
| W | 40.5 g |
| WB | 40.2 g |
| WY | 38.1 g |
| WYB | 51.6 g |

The WB and WY samples showed no more ethanol production than the W sample and hardly any more ethanol production than the C sample. Surprisingly, the WYB sample produced significantly more ethanol than any other sample, showing the advantageous use of the combination of YPD media and BacLyte in pre-fermentation over the use of either separately.

The volume of low wines produced during the subsequent processing and the alcohol by volume of the low wines is set out in table 4:

TABLE 4

| Sample | Volume (ml) | Alcohol by Volume (%) |
|---|---|---|
| C | 950 | 13.9% |
| W | 920 | 13.0% |
| WB | 995 | 13.4% |
| WY | 905 | 13.9% |
| WYB | 910 | 14.9% |

The WYB sample produced a low wine of significantly higher alcohol by volume than any other sample. It is noted that the WB and WY samples produced low wines with an alcohol by volume no higher than that of the control sample.

The volume of the hearts produced during the subsequent processing and the alcohol by volume of the hearts is set out in table 5:

TABLE 5

| Sample | Volume (ml) | Alcohol by Volume (%) | Alcohol volume (ml) |
|---|---|---|---|
| C | 81 | 58.3% | 47.2 |
| W | 102 | 54.9% | 56.0 |
| WB | 77 | 59.9% | 46.1 |
| WY | 79 | 59.9% | 47.3 |
| WYB | 95 | 59.8% | 56.8 |

It is believed that the result for the W sample in table 5 is anomalous. This is because the volume of liquid produced and the alcohol by volume of this sample is not in keeping with any of the WB, WY, or C samples. Further, in contrast to all of the other samples, the alcohol by volume of the W low wine sample is significantly below 60% and the volume of low wine is similar to that of the W, WY and WYB samples and significantly lower than either the C or WB samples. As such one would not reasonably expect such a high volume for W in Table 5. In addition, in contrast to all of the other samples, the amount of alcohol in the W sample is not in keeping with the theoretical alcohol yield set out above in table 3. This indicates that there could have been methodological issues in producing the hearts from the W sample and the result of the W sample shown in table 5 is not correct.

If the W sample is accepted to be anomalous, the hearts of the WYB sample have an alcohol volume more than 20% greater than the other samples. Most surprisingly, the hearts of the WYB sample have an alcohol volume 20% greater than either the WY or the WB sample, which is something that would not be expected from the disclosure of the prior art.

Subsequently the contents of each of the hearts was analysed for higher alcohol content using gas chromatography with flame ionisation detector (GC-FID). The results of this analysis is set out in table 6. This table shows the contents of each heart in ng/μl:

TABLE 6

| Component | C | W | WB | WY | WYB |
|---|---|---|---|---|---|
| Acetaldehyde | 235.89 | 290.13 | 440.21 | 232.50 | 167.81 |
| Ethyl acetate | 1176.68 | 827.29 | 1814.29 | 1940.09 | 4235.89 |
| Isoamyl acetate | 4305.99 | 3983.07 | 5883.56 | 6019.06 | 5915.97 |
| n-Butanol | 196.97 | 172.68 | 185.78 | 193.34 | 159.31 |
| Pentanol | 5361.71 | 5715.15 | 6248.46 | 6127.21 | 5926.81 |
| Furfural | 665.16 | 930.98 | 441.22 | 535.93 | 538.65 |
| n-Propanol | N/D | N/D | N/D | 3099.78 | 385.327 |

Most significantly, the amount of ethyl acetate is more than double in the WYB sample than any other sample, and four times that of the W sample.

In FIG. 7 the theoretical effect of the method of fermentation of the present invention is set out. In particular, the theoretical ethanol concentration over time for four separate bulk fermentation mixtures is shown. The four bulk fermentation mixtures are as follows:

i) Mixture comprising yeast that has not been pre-fermented to form an enhancement mixture;
ii) Mixture comprising an enhancement mixture in which yeast has been hydrated with a YPD media only;
iii) Mixture comprising an enhancement mixture in which yeast has been hydrated with BacLyte only;
iv) Mixture comprising an enhancement mixture in which yeast has been hydrated with BacLyte and a YPD media, in accordance with the present invention.

Figure 9:
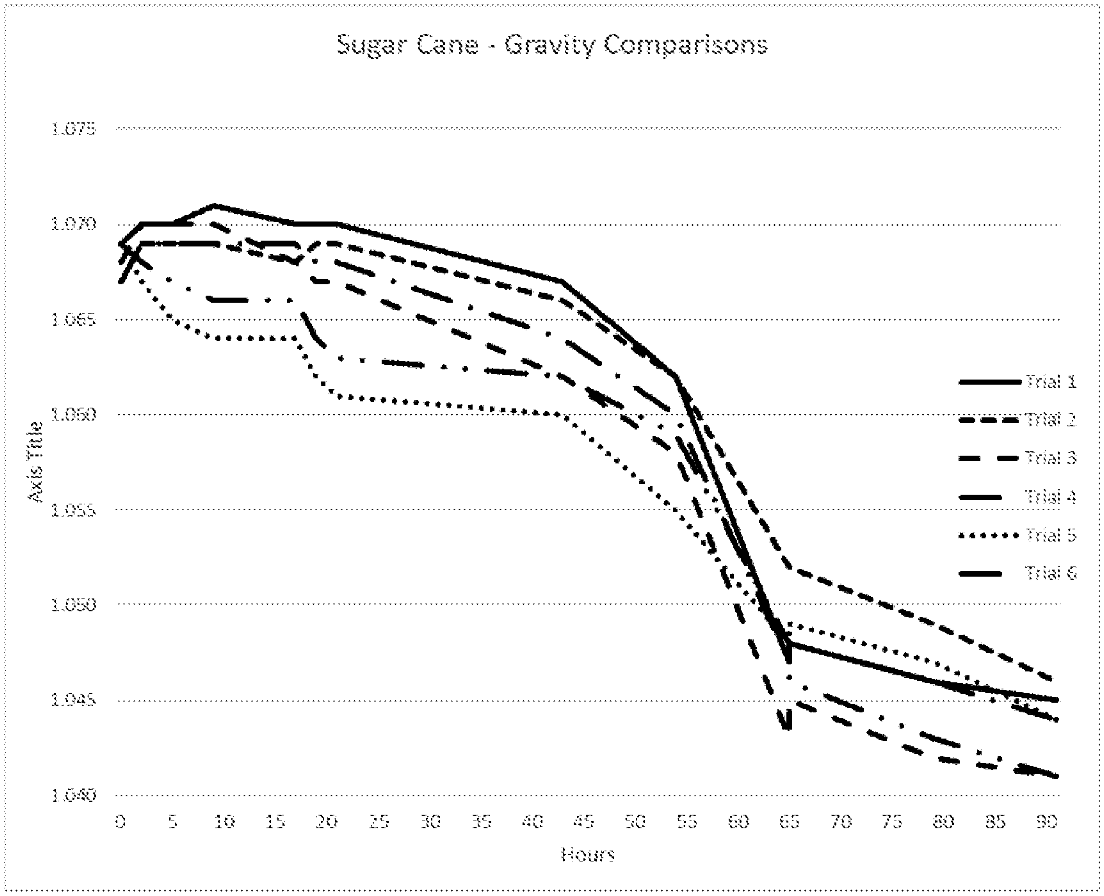
FIG. 9 is a graph showing the specific gravity over time for the sugar cane trials of the second investigation described below.

One of the reasons for the limitation on ethanol yields from bulk fermentations is the toxicity of alcohol on yeast. In conventional fermentations when the alcohol content of the bulk fermentation mixture reaches 8.5% the bulk fermentation mixture becomes toxic to the yeast and fermentation ceases. Therefore, as shown in FIG. 9, the maximum ethanol yield of bulk fermentation mixtures in which the yeast has not been exposed to BacLyte is likely to be 8.5%.

BacLyte appears to have mode of action that acts upon the stress response of yeast. In particular, BacLyte appears to allow yeast to tolerate higher alcohol concentrations of up to 10%. This is shown in the maximum ethanol concentrations of the bulk fermentation mixtures of FIG. 7. Thus, the use of BacLyte in pre-fermentation mixtures is expected to increase the efficiency of bulk fermentation.

The effect of the use of the pre-incubation is also shown by comparing mixture i) with mixtures ii), iii), and iv). In particular, in mixture i) there is an initial time-lag of around 6 hours whilst the yeast propagates within the bulk fermentation mixture. If an enhancement mixture is used in accordance with the present invention then this time-lag is eliminated as the yeast has already propagated.

In addition it is expected that pre-incubation of yeast with BacLyte results in increased fermentation rates of bulk fermentation mixtures as compared to fermentation of bulk fermentation mixtures without BacLyte. This is because of the increased metabolic activity of yeast in the presence of BacLyte. This can be seen by comparing the fermentation rates of mixtures iii) and iv) with the fermentation rates of mixtures i) and ii).

In summary, fermentation according to the present invention utilising an enhancement mixture prepared according to the present invention is expected to provide higher ethanol yields at a quicker rate, as compared to either traditional fermentation methods or prior art fermentation methods utilising enhancement mixtures.

In particular, as shown in the data above at table 3, the theoretical ethanol yield of a bulk fermentation mixture utilising an enhancement mixture according to the present invention has been found to be 25% higher than the theoretical ethanol yield than bulk fermentation mixtures utilising hydrated yeast according to the prior art. Hydrated yeast according to the prior art includes yeast hydrated in water alone, yeast hydrated with only BacLyte and water, and yeast hydrated with only YPD media.

SECOND INVESTIGATION

Figure 8:
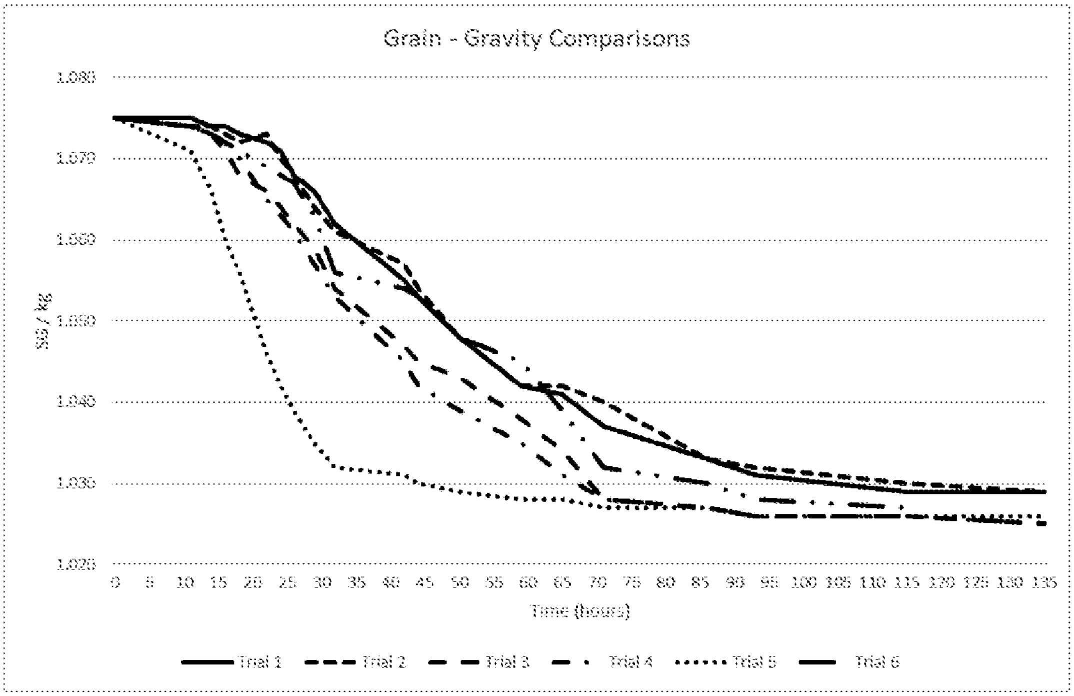
FIG. 8 is a graph showing the specific gravity over time for the grain trials of the second investigation described below.

The results of a second investigation into the use of BacLyte and a banana extract to form an enhancement mixture with alternative sugar sources are shown in FIGS. 8 and 9. In particular, the following second investigation was carried out:

Yeast was hydrated in accordance with the hydration protocol set out in Hornig, J (2019) "A study into the efficacy of hydration regimes & novel nutrient-rich media on yeast propagation, fermentative activity and distillate composition in potato-based Spirit" MSc dissertation [2018-2019] The School of Engineering and Physical Sciences ("Hornig et al.). The second investigation was performed with a different sugar source to the potato feedstock utilised in Hornig et al. with these tests looking at the effects of "Propagreater" and a banana extract in grain and sugar cane fermentations Materials:

- Yeast Pinnacle MG+ (fresh crumbles);
- "Propagreater": a supplement consisting of a 5× concentrate of Yeast Peptone Dextrose (YPD) media and 25% Baclyte;
- Banana extract;
- Yeast Peptone Dextrose (YPD) media solution;
- Feedstock:
  - Grains (rye, wheat and barley) or,
  - Sugar cane.

The yeast was hydrated for 6 hours at 35° C. with a ratio of 1:50 (v/v) of yeast:water. The yeast used was fresh Pinnacle MG+ acclimatised to fermentation temperature, with 2 g/L pitching rate.

Six trials were carried out as follows:

- Trial 1 Direct yeast pitch
- Trial 2 6 hours incubation in water
- Trial 3 6 hours incubation in 1×YPD media
- Trial 4 6 hours incubation in 1× concentrate of YPD and banana supernatant 5%
- Trial 5 6 hours incubation in "Propagreater" supplement (a 5× concentrate of YPD and 25% Baclyte) diluted with 4 parts water to make it 1×YPD plus 5% Baclyte
- Trial 6 6 hours incubation in water and banana supernatant 5%

Grain Fermentation

Set 1 of fermentations was performed with a base of finely milled 70% rye, 20% wheat and 10% malted barley, saccharification at 62° C. for 1 hour with exogenous amylase, glucoamylase and cellulase, cooled down to 25° C. before pitching the yeast into the fermentation. pH 5.2 The results of this set is shown in FIG. 1.

Comparing each trial, we can see trial 5 (hydrated with "Propagreater") having a much shorter lag phase and overall fermentation profile as compare to pitching with either the dry yeast or water hydrated yeast controls. Similarly trials 3 and 4 show a noticeable, yet much less rapid, gravity decrease which suggests a positive impact of pre-treatment with YPD with or without the banana extract in hydration phase. Pre-treatment of yeast with banana extract (trial 6) also showed a positive effect but significantly less than either YPD alone or when it is used in combination with YPD.

Overall, this data demonstrates that "Propagreater" as having a significant impact in reducing the lag phase of the fermentation and the significantly accelerated drop in specific gravity is indicative of accelerated alcohol production. The data also suggests similar utility for the combination of YPD and Banana extract—albeit with significantly less dramatic improvements in the yeast's performance or rate of alcohol synthesis (as shown by decreasing specific gravity). In this grain fermentation the presence of banana in the pre-treatment effected a further drop in specific gravity which is indicative of a higher level of alcohol in the final fermentate.

Using the known calculation for conversion of specific gravity to percentage alcohol by volume:

Subtract the Original Gravity from the Final Gravity.

Multiply this number by 131.25.

The resulting number is your alcohol percent, or ABV %

We are able to calculate the theoretical values of final % ABV for "Propagreater" as being 6.43%, for YPD plus 5% Banana Extract as being 6.56% over the dry yeast and water hydrated control values of 6.04%. This gives a theoretical improvement of alcohol yield from these fermentations as being 6.4% with pre-treatment with "Propagreater" and 8.6% with pre-treatment with YPD plus Banana Extract.

Sugar Cane Fermentation:

These fermentations were performed with a base of sugar cane boiled yeast nutrient and citric acid for ph correction (pH 5.2), cooled down to 25° C. before pitching the yeast. Six trials were carried out, in accordance with the method for the grain fermentation set out above. The only difference being the sugar source for the fermentations being a sugar cane source, rather than a grain source. The results of the trials are shown in FIG. 8.

Comparing each trial, it can be seen that trial 4 (hydrated with YPD and banana extract) and trial 5 (hydrated with "Propagreater") demonstrate specific gravity reducing much more rapidly than the dry yeast (Trial 1) and water hydrated (Trial 2) controls. Trials 1, 2 and 3 show a longer lag phase than trails 4, 5 and 6—all of which see the yeast pre-treated with either Baclyte (in the "Propagreater" formulation) or the banana extract. This clearly demonstrates the effect that the presence of Baclyte or banana extract in the pre-treatment results in increased metabolic activity of the yeast.

These tests prove the utility of "Propagreater" and banana extract plus YPD to improve fermentation efficiency and yield across multiple feedstocks. The improved effect occurring with both grain and sugar cane sources, in addition to the potato fermentation illustrated in FIGS. 1 and 6 and described above.

Pre-treatment with "Propagreater" brings about a beneficial effect in shortening lag phase and accelerating the fermentation. "Propagreater" demonstrated the highest performance in improving fermentation speed and the presence of the cruder banana extract in hydration phase also brought about greater decreases in specific gravity. Calculations of alcohol yield from final specific gravities demonstrates the effect of YPD plus banana extract or "Propagreater" (YPD plus Baclyte) as having a positive effect in terms of overall yield.

THIRD INVESTIGATION

A third investigation into the use of BacLyte and a banana extract to form an enhancement mixture was carried out.

Yeast was hydrated in accordance with the hydration protocol set out in Hornig, J (2019) "A study into the efficacy of hydration regimes & novel nutrient-rich media on yeast propagation, fermentative activity and distillate composition in potato-based Spirit" MSc dissertation [2018-2019] The School of Engineering and Physical Sciences ("Hornig et al.).

Materials:

HG-1 Yeast

"Propagreater": a supplement consisting of a 5× concentrate of Yeast Peptone Dextrose (YPD) media and 25% Baclyte;

Banana extract;

Yeast Peptone Dextrose (YPD) media solution;

Feedstock: potato mash

Six trials were carried out as follows:

TABLE 7

| | | | |
|---|---|---|---|
| Control | Yeast HG-1 | 0.5 g | Incubated for 6 |
| | Water (30 degrees) | 5 ml | hours at 30 degrees |
| | Enzyme Treated Mash | 750 ml | |
| | AntiFoam | 0.2 ml | |
| Trial 1 | Yeast HG-1 | 0.5 g | Incubated for 6 |
| | YPD | 1 ml | hours at 30 degrees |
| | Water (30 degrees) | 4 ml | |
| | Enzyme Treated Mash | 750 ml | |
| | AntiFoam | 0.2 ml | |
| Trial 2 | Yeast HG-1 | 0.5 g | Incubated for 6 |
| | Propagreater | 1 ml | hours at 30 degrees |
| | Water (30 degrees) | 4 ml | |
| | Enzyme Treated Mash | 750 ml | |
| | AntiFoam | 0.2 ml | |
| Trial 3 | Yeast HG-1 | 0.5 g | Incubated for 6 |
| | 20% Banana Extract | 1 ml | hours at 30 degrees |
| | YPD | 1 ml | |
| | Water (30 degrees) | 3 ml | |
| | Enzyme Treated Mash | 750 ml | |
| | AntiFoam | 0.2 ml | |

TABLE 7-continued

| | | | |
|---|---|---|---|
| Trial 4 | Yeast HG-1 | 0.5 g | Incubated for 6 |
| | 5% Banana Extract | 250 microliters | hours at 30 degrees |
| | YPD | 1 ml | |
| | Water (30 degrees) | 3.8 ml | |
| | Enzyme Treated Mash | 750 ml | |
| | AntiFoam | 0.2 ml | |
| Trial 5 | Yeast HG-1 | 0.5 g | Incubated for 6 |
| | 5% BacLyte | 250 microliters | hours at 30 degrees |
| | YPD | 1 ml | |
| | Water (30 degrees) | 3.8 ml | |
| | Enzyme Treated Mash | 750 ml | |
| | AntiFoam | 0.2 ml | |

Each trial was incubated for 6 hours at 30 degrees in a water bath, in a 50 ml conical incubation vessel. After this incubation period the additions were pitched into a 1000 ml conical fermenter along with 750 ml of enzyme treated and crash cooled potato mash. These were then tested for density, pH, alcohol and sealed with one-way breathers that were sealed with antibacterial solution. From pitching the trials were then tested every 6 hours to determine the rate and growth of the ferments until completion. Upon completion, each ferment was stored at 2 degrees to stop any more malolactic fermentation or esterification before being vacuum distilled at 97 mbar to distil all the ethanol content to compare LPA yield from trial to trial.

The results of the third investigation are as follows:

TABLE 8

| | Final Gravity: | Final ABV: | mLPA: | Final pH: |
|---|---|---|---|---|
| Control | 1.0026 | 7.14% | 53.55 | 4.09 |
| Trial 1 | 1.0027 | 7.13% | 53.48 | 4.22 |
| Trial 2 | 1.0017 | 7.52% | 56.40 | 4.24 |
| Trial 3 | 1.0014 | 7.56% | 56.70 | 4.20 |
| Trial 4 | 1.0011 | 7.60% | 57.00 | 4.14 |
| Trial 5 | 1.0020 | 7.48% | 56.10 | 4.12 |

The specific gravity of the trials over time was as follows:

TABLE 9

| Time | 0 hrs | 6 hrs | 12 hrs | 18 hrs | 24 hrs | 30 hrs | 36 hrs | 38.1 hrs |
|---|---|---|---|---|---|---|---|---|
| Control | 1.053 | 1.0498 | 1.0428 | 1.0326 | 1.0281 | 1.0167 | 1.0056 | 1.0026 |
| Trial 1 | 1.053 | 1.0422 | 1.0356 | 1.0281 | 1.0267 | 1.0155 | 1.0082 | 1.0027 |
| Trial 2 | 1.053 | 1.0392 | 1.0349 | 1.0273 | 1.0229 | 1.0122 | 1.0069 | 1.0017 |
| Trial 3 | 1.053 | 1.0382 | 1.0331 | 1.0277 | 1.0237 | 1.0127 | 1.0049 | 1.0014 |
| Trial 4 | 1.053 | 1.0378 | 1.0328 | 1.0269 | 1.0225 | 1.0094 | 1.0032 | 1.0011 |
| Trial 5 | 1.053 | 1.0399 | 1.0347 | 1.0279 | 1.0233 | 1.0157 | 1.0057 | 1.0020 |

The fermentation ABV of the trials over time was as follows:

TABLE 10

| Time | 0 hrs | 6 hrs | 12 hrs | 18 hrs | 24 hrs | 30 hrs | 36 hrs | 38.1 hrs |
|---|---|---|---|---|---|---|---|---|
| Control | 0.02% | 1.21% | 2.13% | 3.46% | 4.13% | 5.55% | 6.49% | 7.14% |
| Trial 1 | 0.04% | 2.20% | 3.07% | 4.06% | 4.24% | 5.71% | 6.67% | 7.13% |
| Trial 2 | 0.04% | 2.60% | 3.16% | 4.16% | 4.74% | 6.14% | 6.84% | 7.52% |
| Trial 3 | 0.02% | 2.73% | 3.40% | 4.11% | 4.63% | 6.08% | 7.10% | 7.56% |
| Trial 4 | 0.05% | 2.78% | 3.44% | 4.21% | 4.79% | 6.51% | 7.32% | 7.60% |
| Trial 5 | 0.02% | 2.51% | 3.19% | 4.08% | 4.69% | 5.68% | 7.00% | 7.48% |

As can be seen, the use of a fermentation enhancement mixture in the present invention is significantly advantageous: it produces a higher ABV more quickly than ethanol enhancement mixtures using YPD as an enhancer only (trial 1).

FOURTH INVESTIGATION

Figure 10:
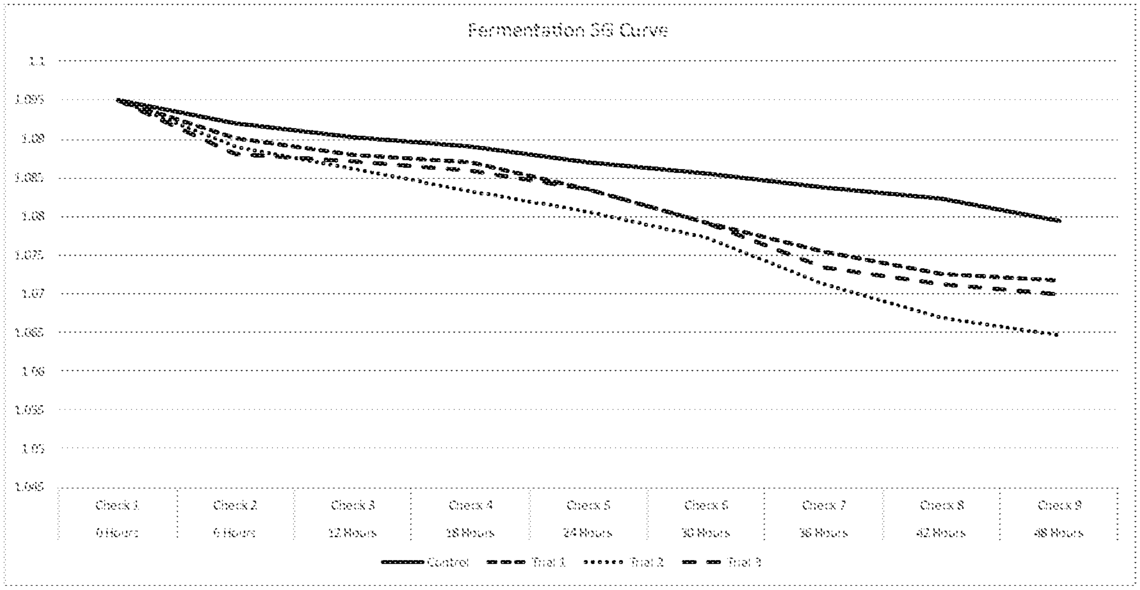
FIG. 10 is a graph showing the specific gravity over time for the trials of fourth investigation described below.
Figure 11:
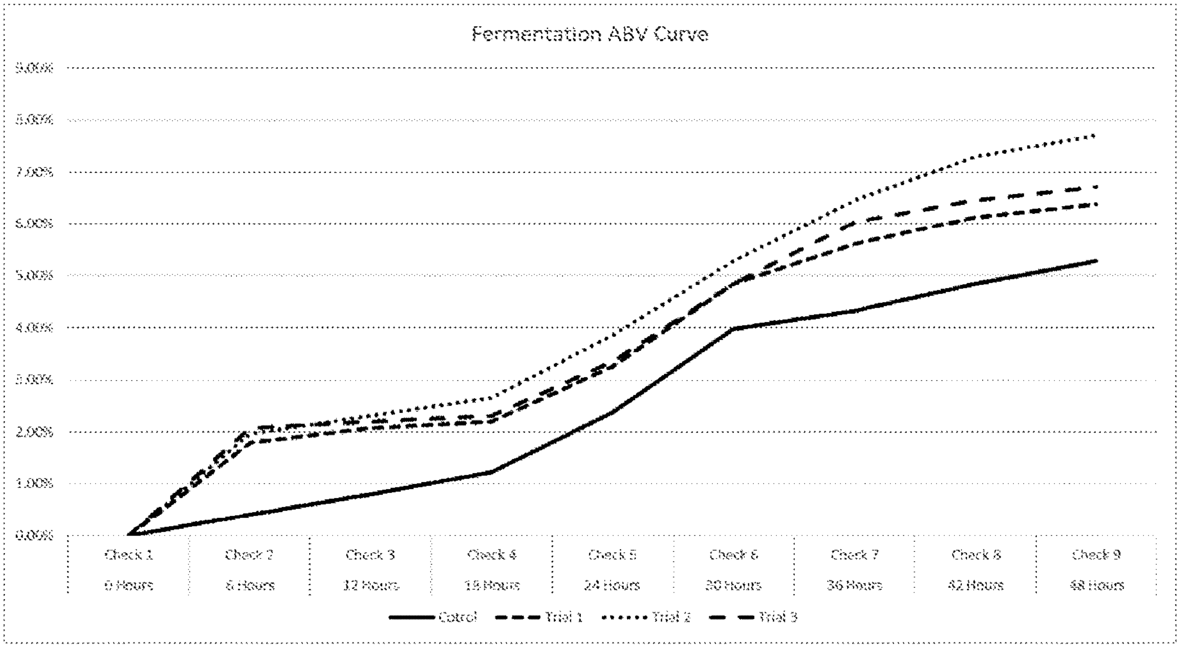
FIG. 11 is a graph showing the alcohol by volume over time for the trials of the fourth investigation described below.

The results of a fourth investigation into the use of BacLyte and a banana extract to form an enhancement mixture with a molasses sugar source are shown in FIGS. 10 and 11. In particular, the following second investigation was carried out.

Four trials were carried out with the following parameters

TABLE 11

| | | | |
|---|---|---|---|
| Control | Yeast C-70 | 0.5 g | Incubated for 6 hours at 30 degrees |
| | Water (30 degrees) | 5 ml | |
| | Molasses | 131.3 ml | |
| | Citric Acid | 1.5 g | |
| | Sugar | 42 g | |
| | Water (80 degrees) | 591 ml | |
| | AntiFoam | 1 ml | |
| Trial 1 | Yeast C-70 | 0.5 g | Incubated for 6 hours at 30 degrees |
| | 20% Banana Extract | 1 ml | |
| | YPD | 1 ml | |
| | Water (30 degrees) | 4 ml | |
| | Molasses | 131.3 ml | |
| | Citric Acid | 1.5 g | |
| | Sugar | 42 g | |
| | Water (80 degrees) | 591 ml | |
| | AntiFoam | 1 ml | |
| Trial 2 | Yeast C-70 | 0.5 g | Incubated for 6 hours at 30 degrees |
| | "Propagreater" | 1 ml | |
| | Water (30 degrees) | 4 ml | |
| | Molasses | 131.3 ml | |
| | Citric Acid | 1.5 g | |
| | Sugar | 42 g | |
| | Water (80 degrees) | 591 ml | |
| | AntiFoam | 1 ml | |
| Trial 3 | Yeast C-70 | 0.5 g | Incubated for 6 hours at 30 degrees |
| | 5% Banana Extract | 250 microliters | |
| | YPD | 1 ml | |
| | Water (30 degrees) | 3.8 ml | |
| | Molasses | 131.3 ml | |
| | Citric Acid | 1.5 g | |
| | Sugar | 42 g | |
| | Water (80 degrees) | 591 ml | |
| | AntiFoam | 1 ml | |

In particular, the samples set out above were each incubated in 100 ml conical flasks for 6 hours at 30 degrees before being pitched into a specific molasses blend of feed grade molasses, citric acid, water, sugar and anti-foam set out above in Table 11 at 30 degrees before being sealed for fermentation with sterile seals. These were subsequently checked every 6 hours for SG, Brix, pH, ABV and internal temperature. Once fermentation was complete, these were distilled using a Buchi R300 Rotovapor at 97 mbar and 50 degrees to extract ethanol to calculate LPA yield.

The results of the trials are set out below in Tables 12 and 13 and shown in FIGS. 10 and 11.

Specific Gravity:

TABLE 12

| Hours Passed | 0 Hours | 6 Hours | 12 Hours | 18 Hours | 24 Hours | 30 Hours | 36 Hours | 42 Hours | 48 Hours |
|---|---|---|---|---|---|---|---|---|---|
| Check No. | Check 1 | Check 2 | Check 3 | Check 4 | Check 5 | Check 6 | Check 7 | Check 8 | Check 9 |
| Control | 1.095 | 1.092 | 1.0902 | 1.089 | 1.0870 | 1.0855 | 1.0837 | 1.0823 | 1.0794 |
| Trial 1 | 1.095 | 1.0901 | 1.088 | 1.087 | 1.0835 | 1.0792 | 1.0755 | 1.0726 | 1.0717 |
| Trial 2 | 1.095 | 1.089 | 1.0862 | 1.0833 | 1.0806 | 1.0773 | 1.0712 | 1.0669 | 1.0646 |
| Trial 3 | 1.095 | 1.0881 | 1.0871 | 1.0859 | 1.0835 | 1.0792 | 1.0734 | 1.0712 | 1.0699 |

Fermentation ABV:

TABLE 13

| Hours Passed | 0 Hours | 6 Hours | 12 Hours | 18 Hours | 24 Hours | 30 Hours | 36 Hours | 42 Hours | 48 Hours |
|---|---|---|---|---|---|---|---|---|---|
| Check No. | Check 1 | Check 2 | Check 3 | Check 4 | Check 5 | Check 6 | Check 7 | Check 8 | Check 9 |
| Control | 0.00% | 0.40% | 0.80% | 1.23% | 2.37% | 3.98% | 4.33% | 4.85% | 5.28% |
| Trial 1 | 0.00% | 1.79% | 2.08% | 2.20% | 3.25% | 4.85% | 5.62% | 6.13% | 6.38% |
| Trial 2 | 0.00% | 1.97% | 2.31% | 2.66% | 3.85% | 5.28% | 6.46% | 7.30% | 7.71% |
| Trial 3 | 0.00% | 2.08% | 2.20% | 2.31% | 3.35% | 4.85% | 6.04% | 6.46% | 6.72% |

As can be seen, the use of a fermentation enhancement mixture in the present invention is significantly advantageous: it produces a higher ABV than the control with molasses as the sugar source. This also validates the effect of the enhancement mixture of the present invention with molasses as a sugar source. The "Propagreater" mixture (trial 2) produced the highest alcohol ABV and, counterintuitively, the 5% of banana extract of trial 3 was found to be more effective than the 20% of banana extract of trial 1. Therefore, in accordance with the present invention it may be preferable to include an amount of banana extract that is 10% or less.

Preparation of Banana Extract

The banana extract discussed above and in the claims of the present invention may be generally prepared as follows:

i) Peeled bananas stored at −84° C., are removed from the freezer. Keep the bananas in the frozen bag and gently break the bananas buy dropping them approximately a foot from a hard tabletop. The bananas will break easily due to their temperature.

ii) Remove 250 grams of banana pieces for every 100 ml of water used and place on the lab bench onto absorbent paper toweling.

iii) Bananas may remain at room temperature for 25-40 minutes, until softened.

iv) Into a blender that has been cleaned and thoroughly rinsed with distilled water, add the weighed banana pulp and water so that one-half to three-quarters of the blender is filled.

v) Blend the banana pulp/water mixture at the top high speed for 90 seconds.

vi) Following blending, the blended banana puree is poured into centrifuge containers and spun at a speed of at least 3900 rpm, or a higher speed if allowed by the centrifuge, at a temperature of 20° C. for 30 minutes and then decelerated at the lowest rate to ensure gentle braking.

viii) Collecting the supernatant into a large Corning autoclavable 1 L glass bottle with no more than 600 ml in the bottle.

ix). Autoclaving at standard autoclave temperature (121° C., 25 minutes, 20 lbs. pressure) to achieve sterility.

x) Allowing the supernatant to cool for 30-45 minutes and then pouring the supernatant into new, sterile 50 ml polypropylene tubes and subject to a round of centrifugation according to the same parameters for the initial processing of the blended fruit.

xi) Collecting 40 ml of the supernatant into sterile, 50 ml polypropylene tubes and discarding any pelleted solid debris.

This method produces a banana extract in accordance with the present invention and in accordance with EP1945763B1, as discussed above. Any other suitable method for preparing the banana extract of EP1945763B1 disclosed in the patent elsewhere or in EP1945763B1 may be used as an alternative for the methods of the present invention.

The invention claimed is:

1. A fermentation method comprising the steps of:

preparing an ethanol fermentation enhancement mixture by (i) hydrating a dried yeast with at least 0.1% Baclyte or 0.1% of a banana extract by volume, and a yeast growth media, to produce a pre-fermentation mixture, and (ii) maintaining the pre-fermentation mixture at a temperature between 20° C. and 40° C. for between 30 minutes and 8 hours to form the enhancement mixture;

adding the enhancement mixture to a bulk fermentation mixture containing a sugar source, to form an enhanced bulk fermentation mixture, the sugar source comprising at least one member selected from molasses, potatoes, potato starch, grain, sugar cane, agave, rice, and corn; and maintaining the enhanced bulk fermentation mixture at temperature of between 2° C. and 40° to allow fermentation of the sugar source to ethanol.

2. The fermentation method according to claim 1, wherein the enhanced bulk fermentation mixture is not further supplemented with BacLyte beyond that present in the enhancement mixture.

3. The method according to claim 1, wherein the sugar source is a potato, molasses, grain, or sugar cane.

* * * * *